(12) United States Patent
Arnett

(10) Patent No.: US 9,103,367 B2
(45) Date of Patent: Aug. 11, 2015

(54) POLYAXIAL LOCKING INTERFACE

(71) Applicant: IMDS LLC, Providence, UT (US)

(72) Inventor: Jeffery D. Arnett, Gilbert, AZ (US)

(73) Assignee: IMDS LLC, Providence, UT (US)

(*) Notice: Subject to any disclaimer, the term of this patent is extended or adjusted under 35 U.S.C. 154(b) by 0 days.

(21) Appl. No.: 13/828,584

(22) Filed: Mar. 14, 2013

(65) Prior Publication Data
US 2014/0271028 A1    Sep. 18, 2014

(51) Int. Cl.
F16B 39/00    (2006.01)
F16B 39/28    (2006.01)

(52) U.S. Cl.
CPC ........................ F16B 39/28 (2013.01)

(58) Field of Classification Search
USPC ............... 411/132–133, 166, 167, 168, 259, 411/402–403, 432, 436
See application file for complete search history.

(56) References Cited

U.S. PATENT DOCUMENTS

| | | | |
|---|---|---|---|
| 2,400,318 A * | 5/1946 | Rosan | 411/373 |
| 2,588,372 A * | 3/1952 | Erb | 411/432 |
| 3,408,887 A * | 11/1968 | Villo | 83/140 |
| 5,358,367 A * | 10/1994 | Yang | 411/397 |
| 5,375,956 A * | 12/1994 | Pennig | 411/389 |
| 5,558,674 A | 9/1996 | Heggeness | |
| 5,904,683 A * | 5/1999 | Pohndorf et al. | 606/287 |
| 6,258,089 B1 | 7/2001 | Campbell | |
| 6,296,642 B1 | 10/2001 | Morrison | |
| 6,306,140 B1 | 10/2001 | Siddiqui | |
| 6,322,562 B1 | 11/2001 | Wolter | |
| 6,719,759 B2 | 4/2004 | Wagner | |
| 6,730,091 B1 | 5/2004 | Pfefferle | |
| 6,955,677 B2 | 10/2005 | Dahners | |
| 6,974,461 B1 | 12/2005 | Wolter | |
| 6,976,816 B2 * | 12/2005 | Slesinski et al. | 411/122 |
| 6,997,660 B2 * | 2/2006 | Fedor | 411/383 |
| 7,137,987 B2 | 11/2006 | Patterson | |
| 7,179,260 B2 | 2/2007 | Gerlach | |
| 7,220,263 B2 | 5/2007 | Cordaro | |
| 7,905,909 B2 | 3/2011 | Orbay | |
| 7,922,433 B2 * | 4/2011 | Ricciardo | 411/119 |
| 7,955,364 B2 | 6/2011 | Ziolo | |
| 8,246,661 B2 | 8/2012 | Beutter | |
| 8,337,535 B2 | 12/2012 | White | |
| 8,343,196 B2 | 1/2013 | Schneider | |
| 8,496,694 B2 | 7/2013 | Hashmi | |
| 8,506,607 B2 | 8/2013 | Eckhof | |
| 2007/0043366 A1 | 2/2007 | Pfefferle | |

(Continued)

FOREIGN PATENT DOCUMENTS

DE    4343117 A1    11/1999
EP    1712197        1/2009

(Continued)

Primary Examiner — Roberta Delisle
(74) Attorney, Agent, or Firm — Maywood IP Law; G. Jo Hays; David W. Meibos

(57) ABSTRACT

An interlocking interface retains a screw head in a socket to prevent migration of the screw head out of the socket, or to lock the screw head in the socket. The interlocking interface may retain or lock the screw at various polyaxial angles with respect to the socket. The screw head includes external corrugations. The socket includes an internal corrugated structure which interlocks with the external corrugations of the screw head when the screw is at various polyaxial angles with respect to the socket.

22 Claims, 21 Drawing Sheets

(56) References Cited

U.S. PATENT DOCUMENTS

| | | |
|---|---|---|
| 2008/0140130 A1 | 6/2008 | Chan |
| 2008/0208259 A1 | 8/2008 | Giblert |
| 2008/0234749 A1 | 9/2008 | Forstein |
| 2010/0312286 A1 | 12/2010 | Dell'Oca |
| 2011/0295325 A1 | 12/2011 | Wagner |
| 2011/0301608 A1 | 12/2011 | Roth |
| 2012/0259371 A1 | 10/2012 | Mathieu |
| 2012/0323284 A1 | 12/2012 | Baker |
| 2014/0277180 A1 | 9/2014 | Paolino |
| 2014/0358230 A1 | 12/2014 | Niese |

FOREIGN PATENT DOCUMENTS

| | | |
|---|---|---|
| EP | 2529685 | 12/2012 |
| JP | 2011067642 | 4/2011 |

* cited by examiner

POLYAXIAL LOCKING INTERFACE

BACKGROUND

The present disclosure relates to retention interfaces in medical devices, such as to prevent a screw from migrating, unthreading, "backing out" and the like. This disclosure also relates to interlocking interfaces, such as screw head and device holes, such as bone plate holes. The principles herein are applicable wherever it is desired to prevent a part from migrating relative to a corresponding socket and/or wherever it is desired to lock a part to a socket.

BRIEF DESCRIPTION OF THE DRAWINGS

While examples of the present technology have been shown and described in detail below, it will be clear to the person skilled in the art that variations, changes and modifications may be made without departing from its scope. As such, that which is set forth in the following description and accompanying drawings is offered by way of illustration only and not as a limitation. The actual scope of the invention is intended to be defined by the following claims, along with the full range of equivalents to which such claims are entitled.

In the following Detailed Description, various features are grouped together in several examples for the purpose of streamlining the disclosure. This method of disclosure is not to be interpreted as reflecting an intention that examples of the technology require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

Figure 1:
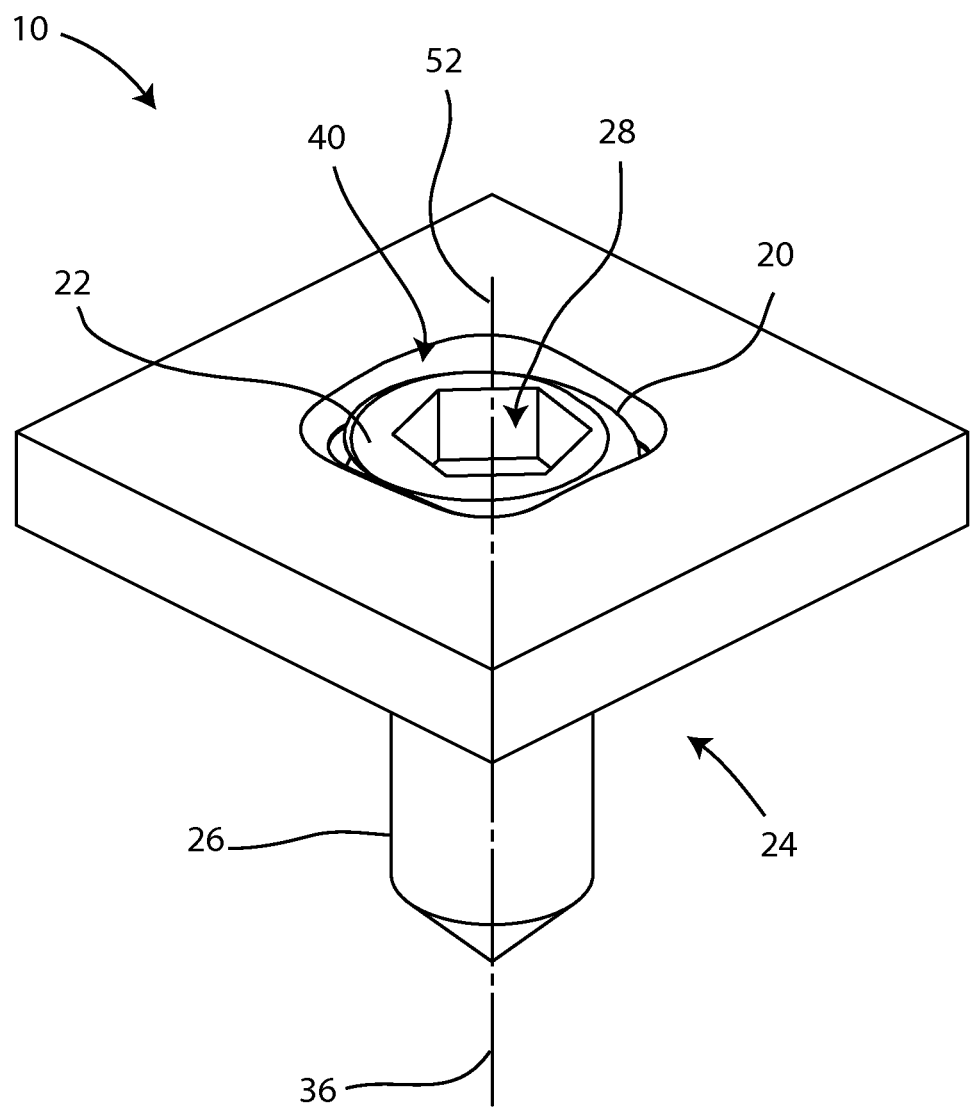

Identical reference numerals do not necessarily indicate an identical structure. Rather, the same reference numeral may be used to indicate a similar feature or a feature with similar functionality. Not every feature of each example is labeled in every figure in which that example appears, in order to keep the figures clear. Similar reference numbers (e.g., those that are identical except for the first numeral) are used to indicate similar features in different examples.

Figure 2:
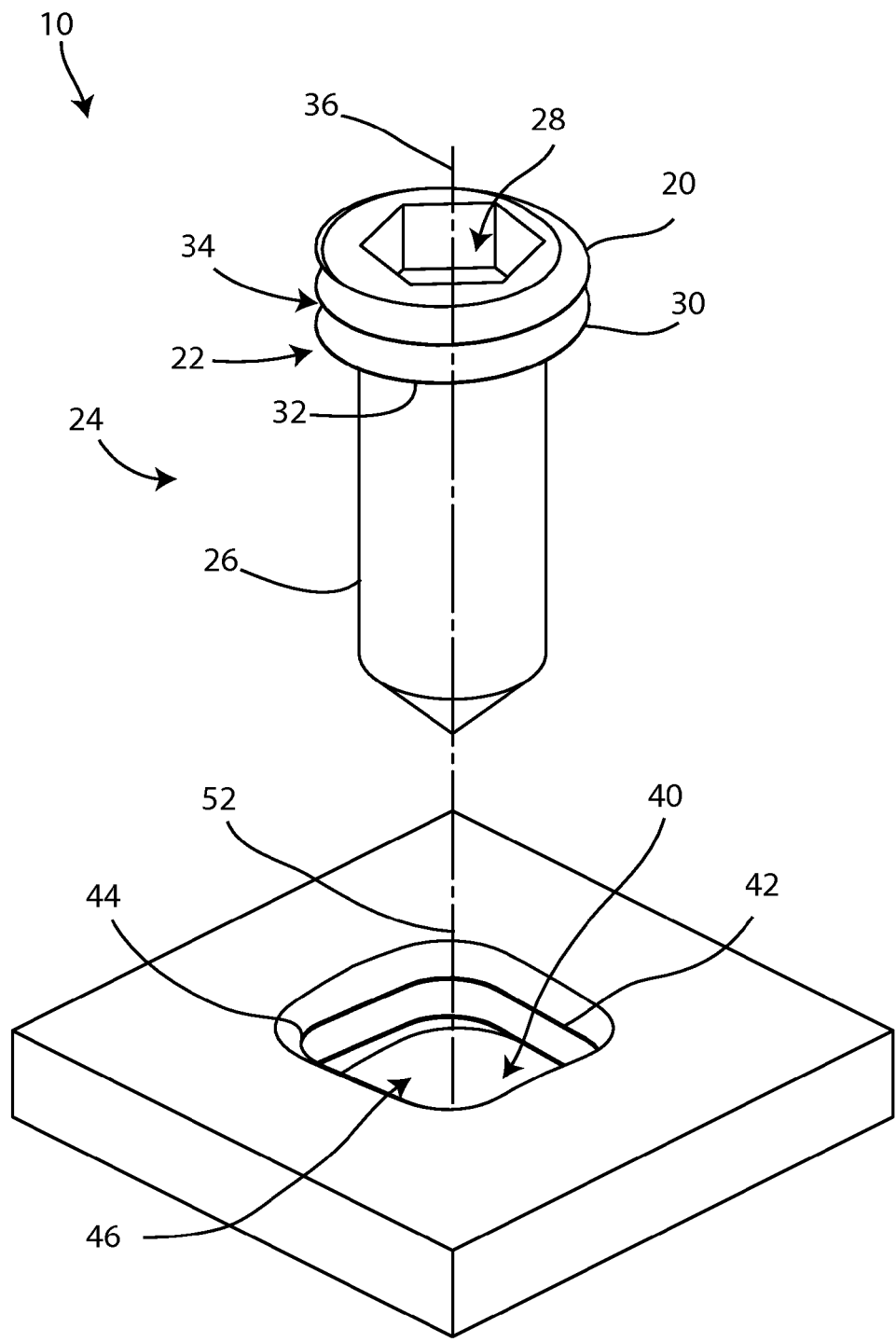
Figure 3:
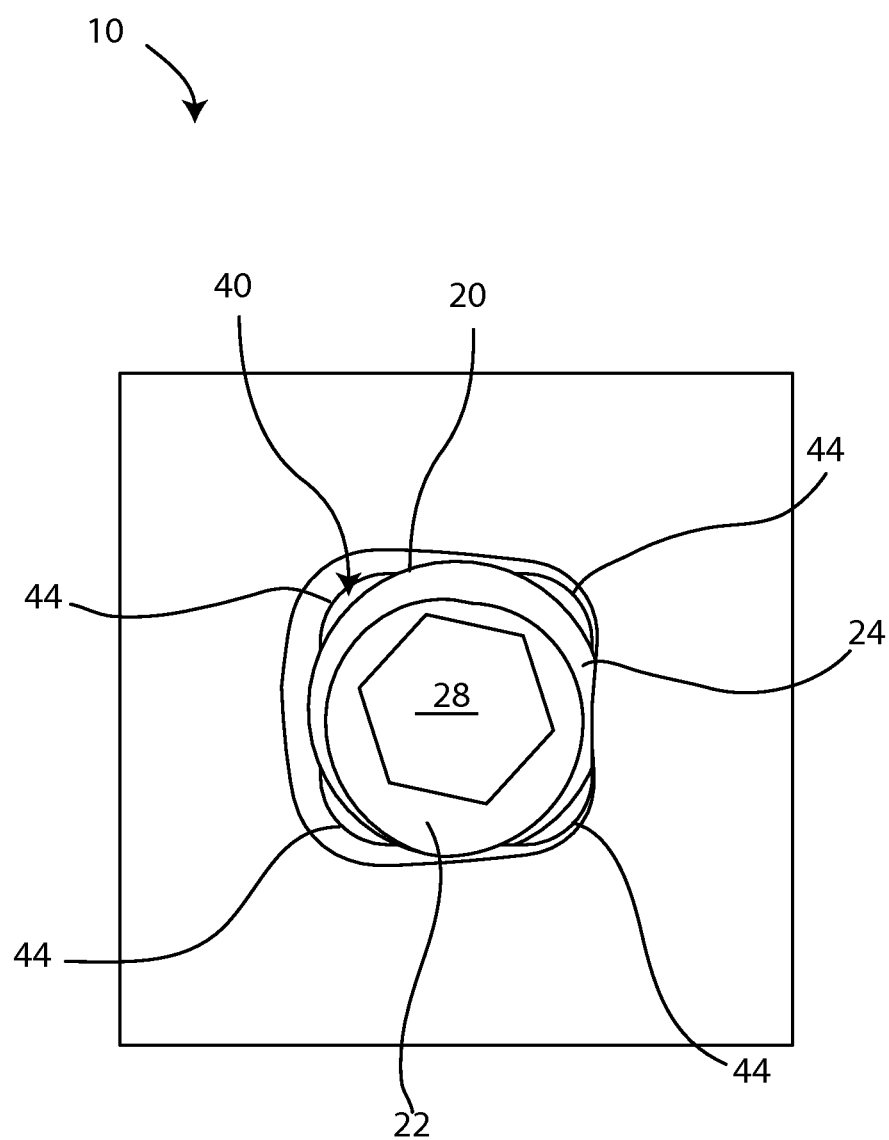
Figure 4A:
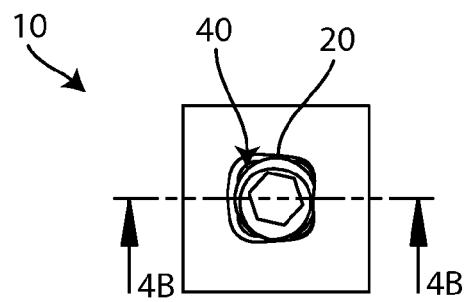
Figure 4B:
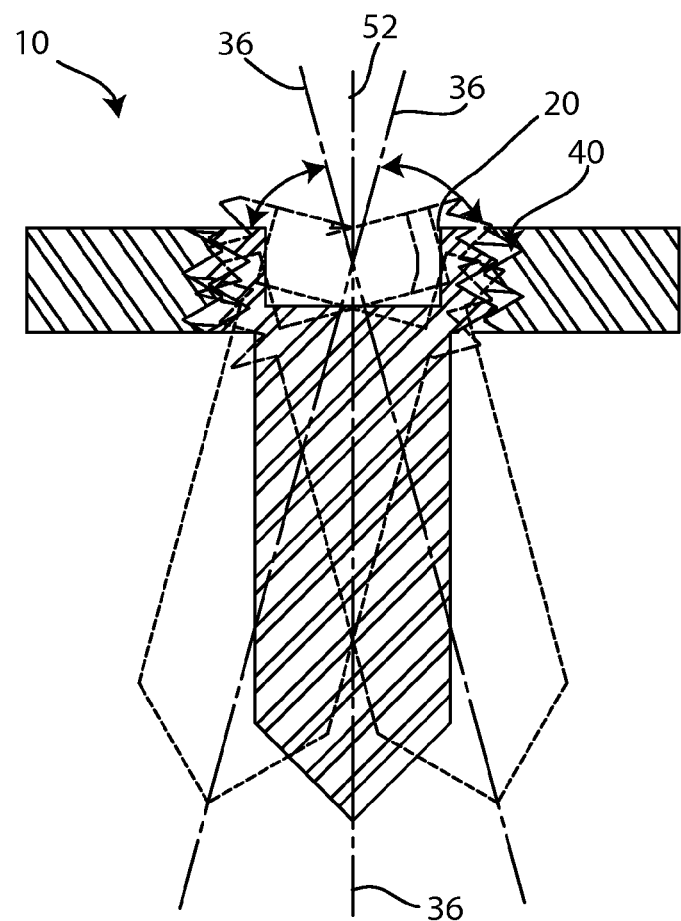
Figure 4:
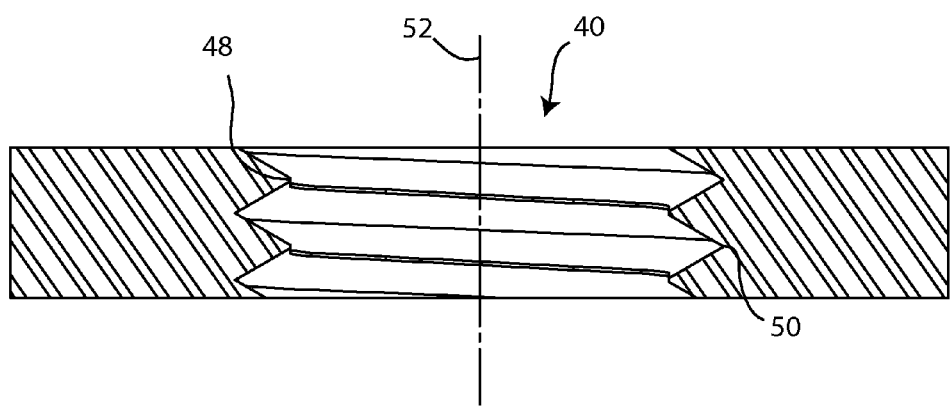
Figure 5:
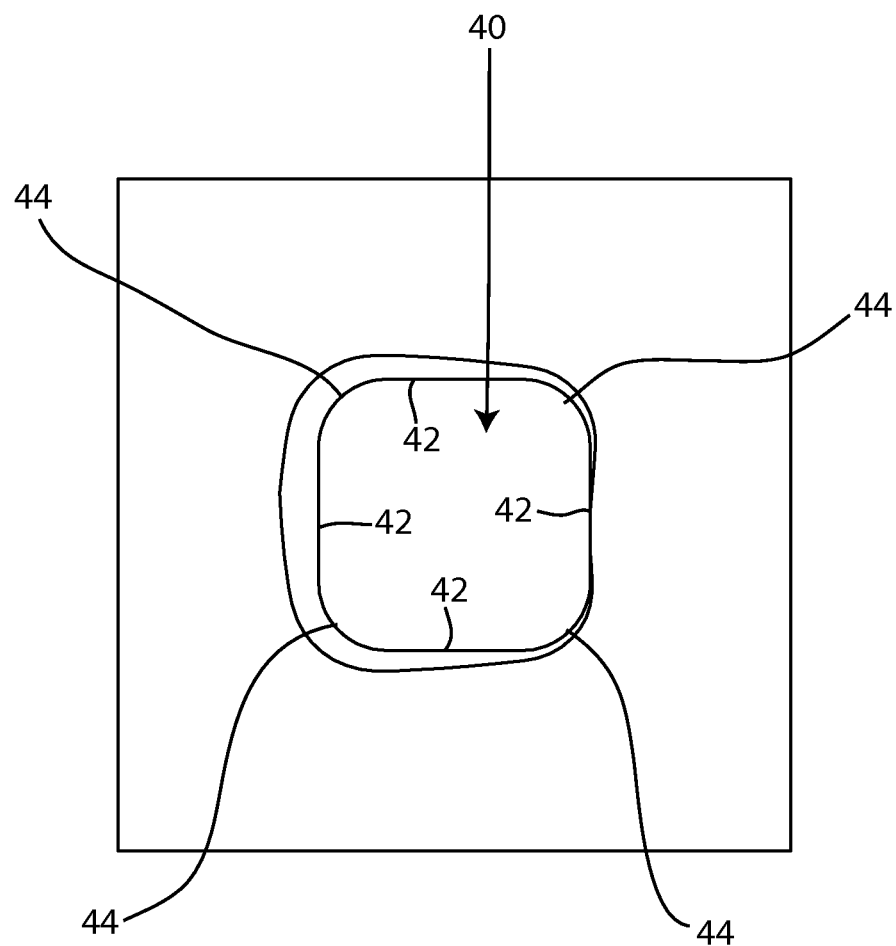
Figure 6:
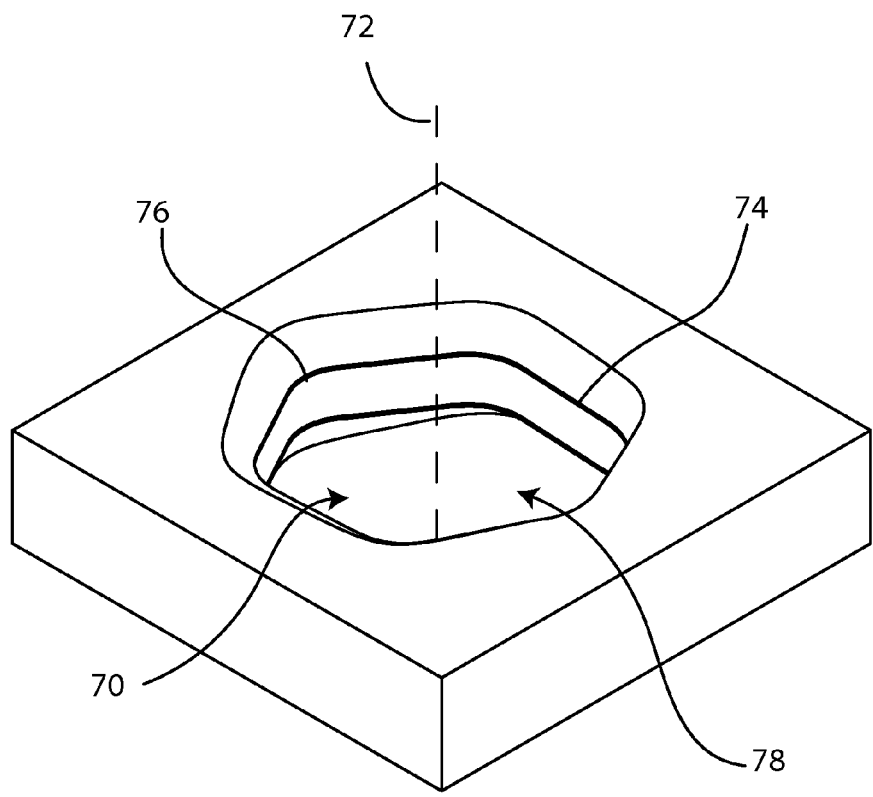
Figure 7A:
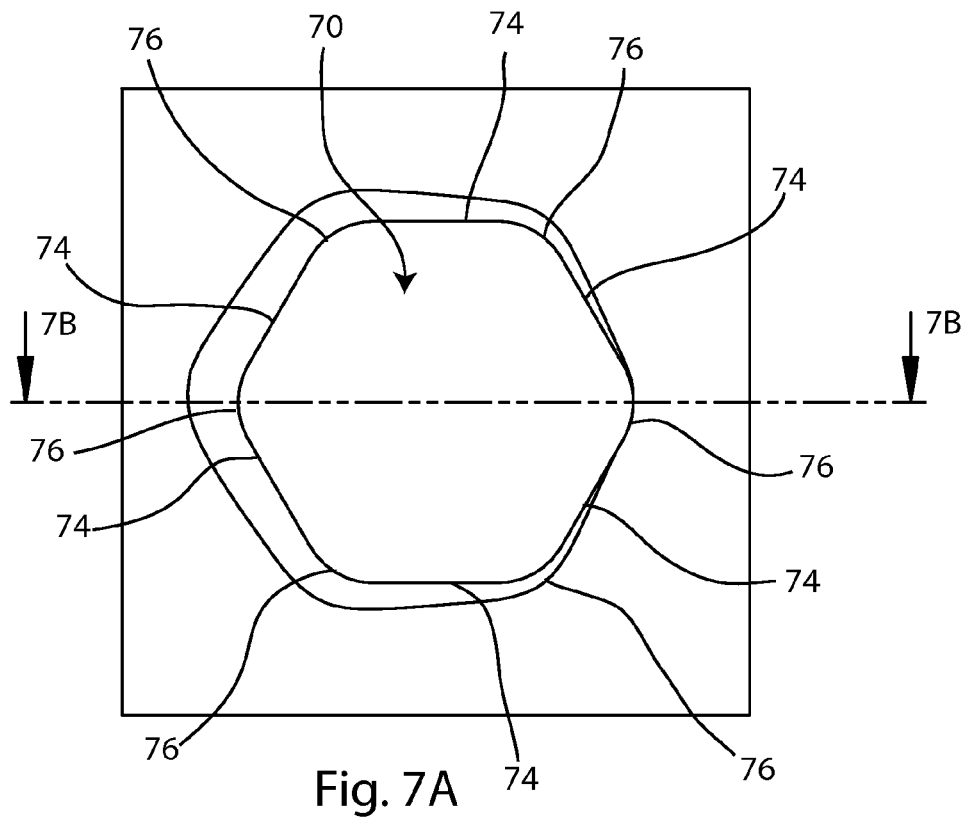
Figure 7B:
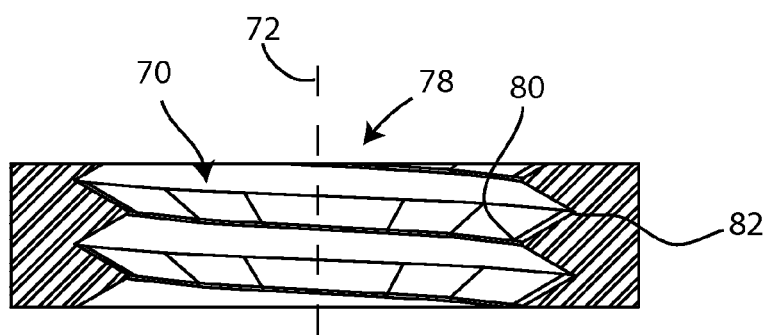
Figure 8:
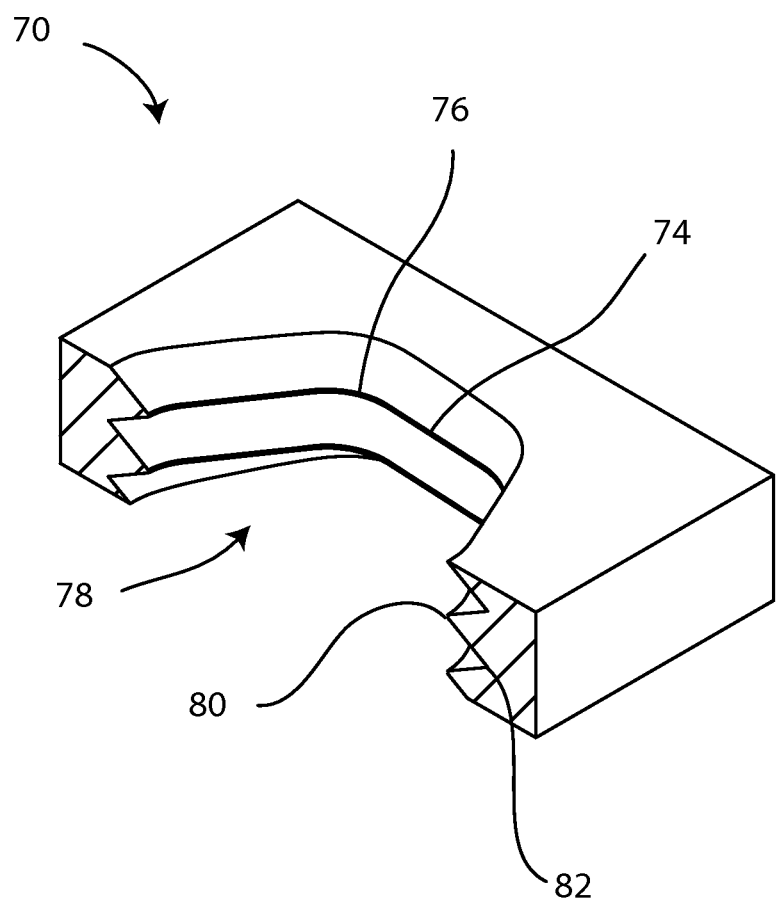
Figure 9:
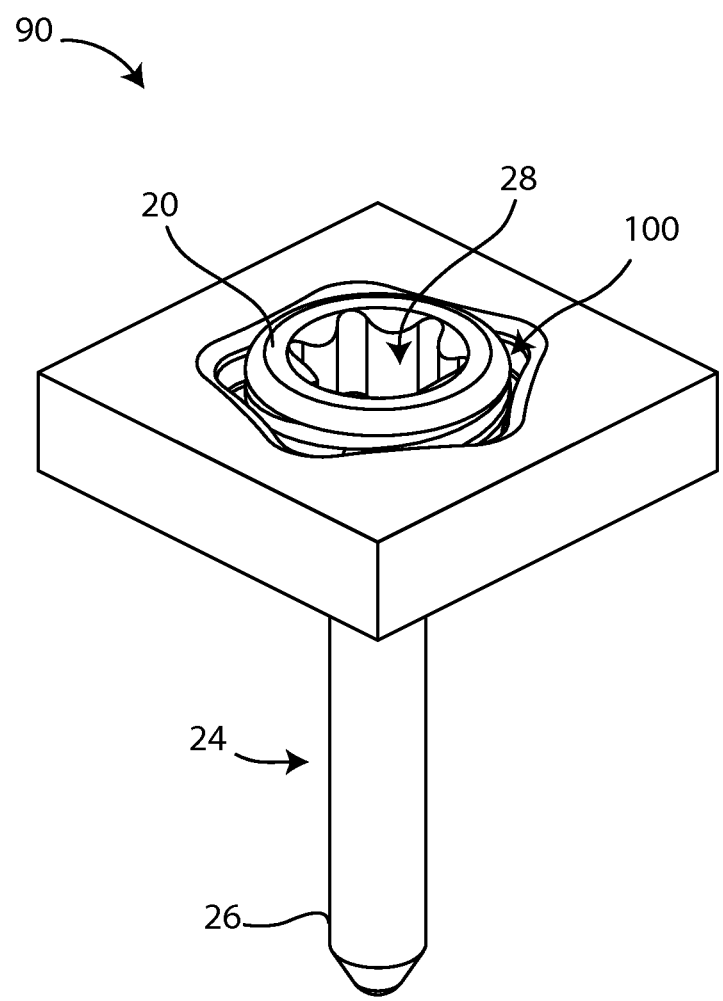
Figure 10:
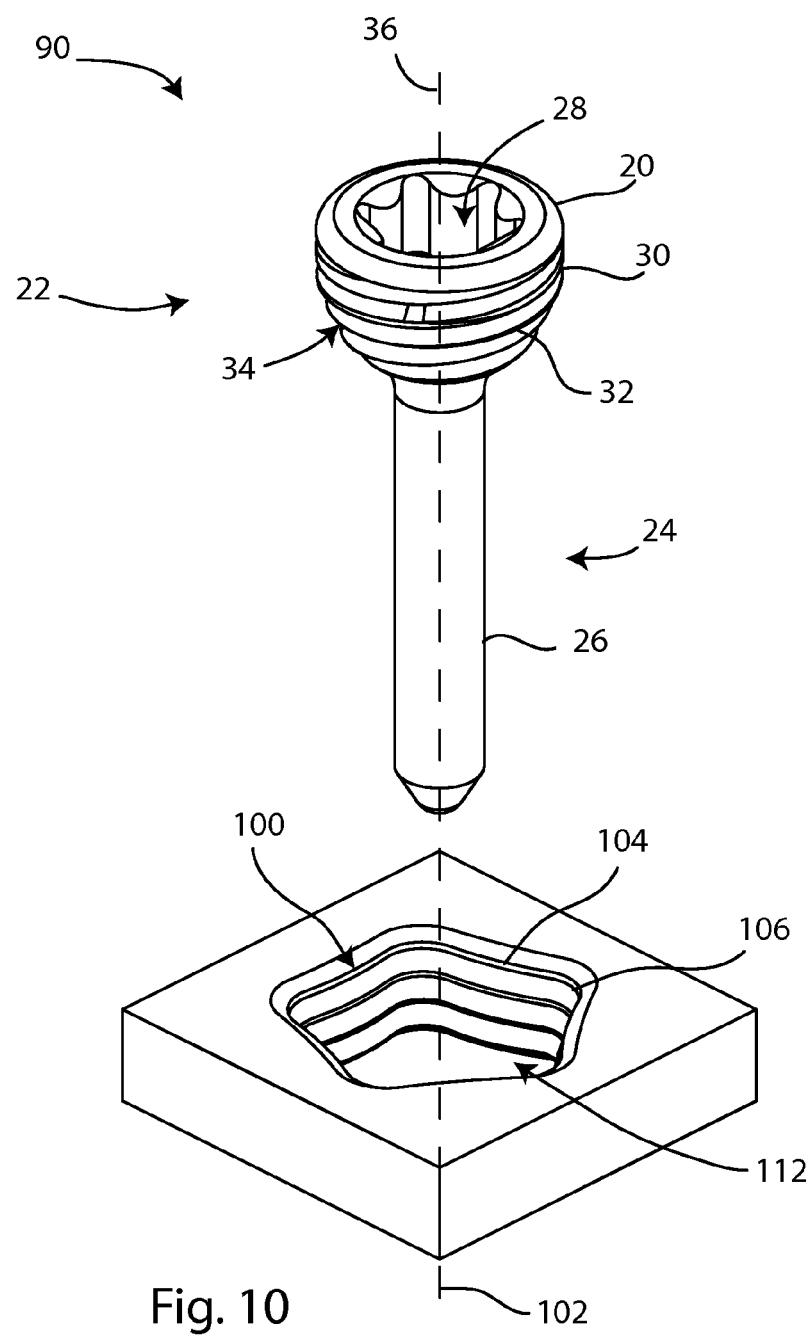
Figure 11A:
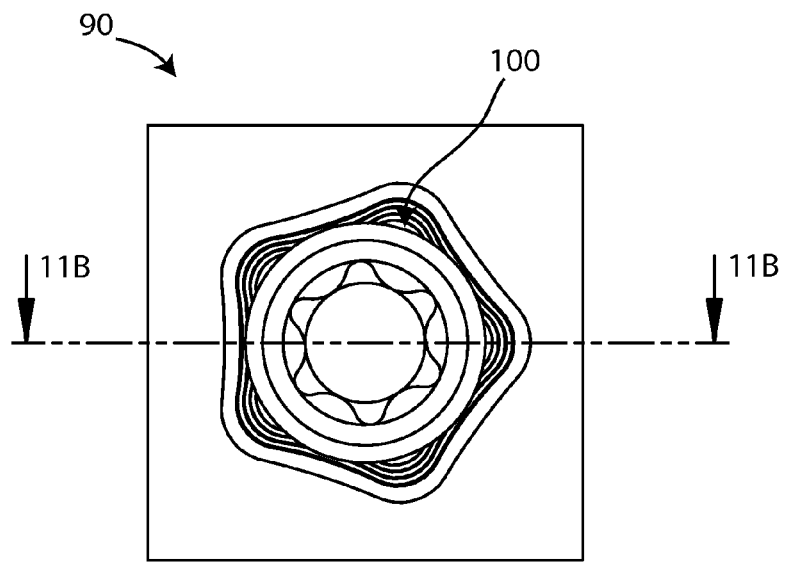
Figure 11B:
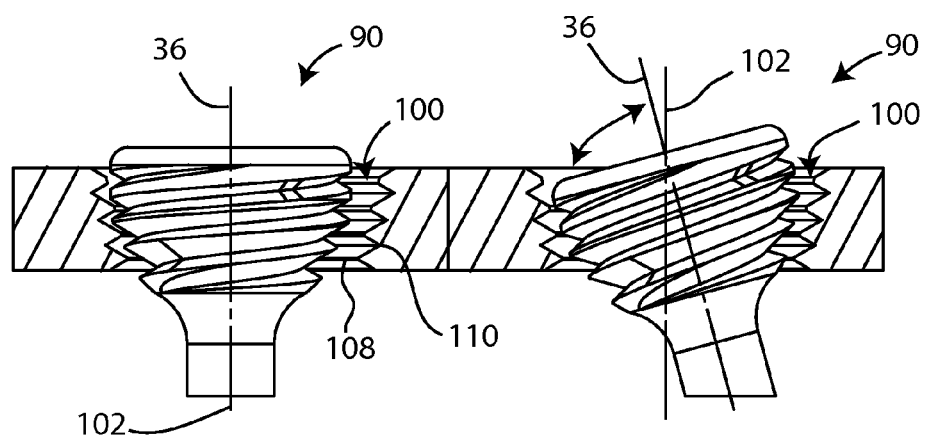
Figure 12:
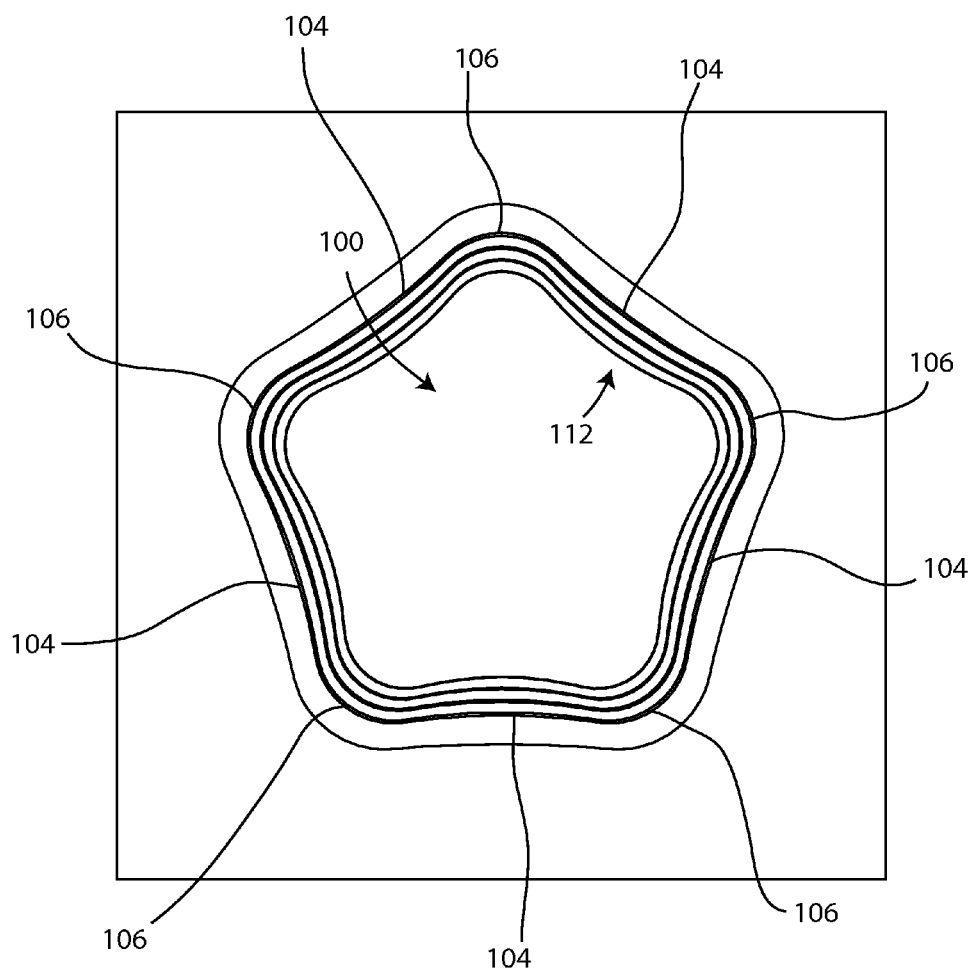
Figure 13:
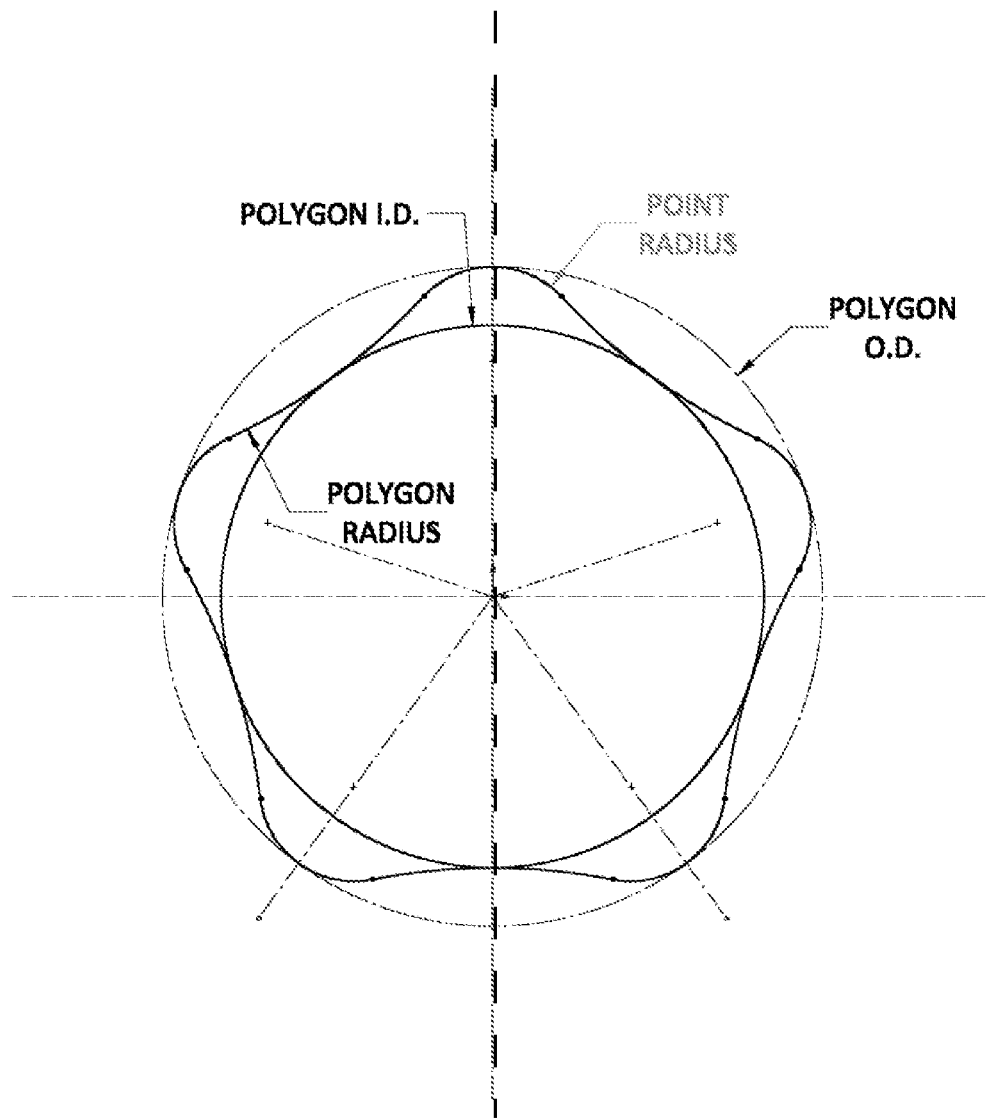
Figure 14A:
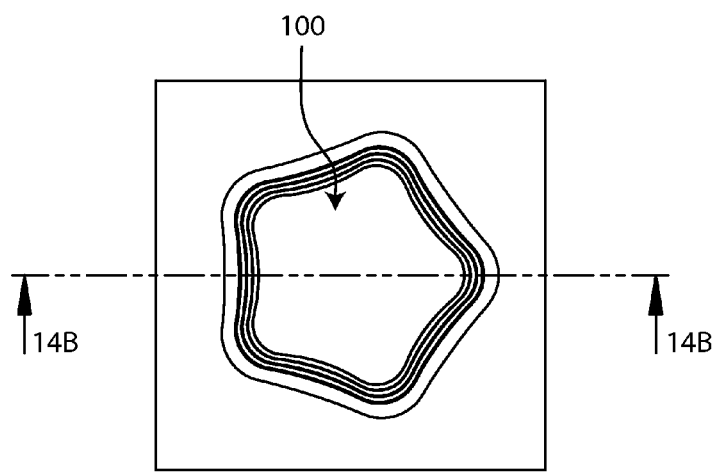
Figure 14B:
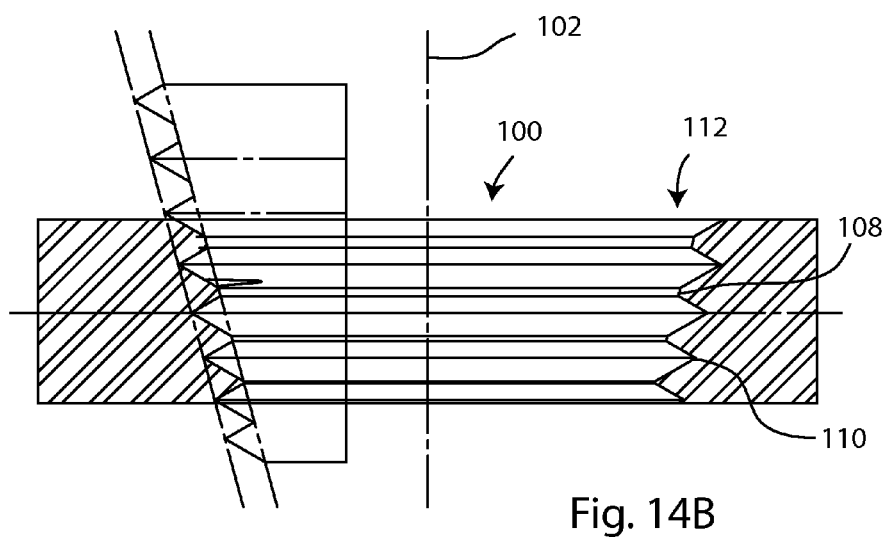
Figure 15A:
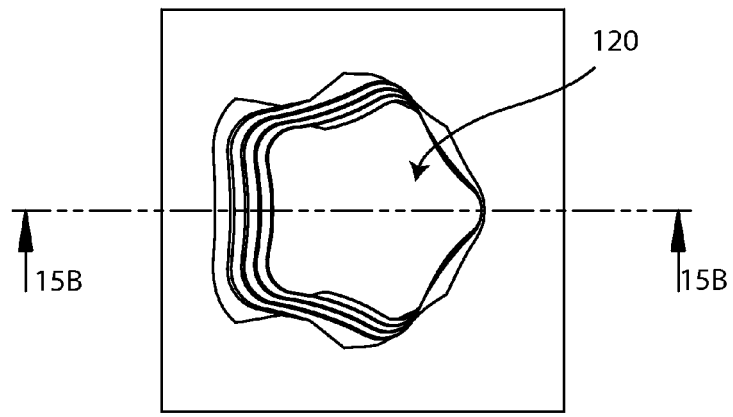
Figure 15B:
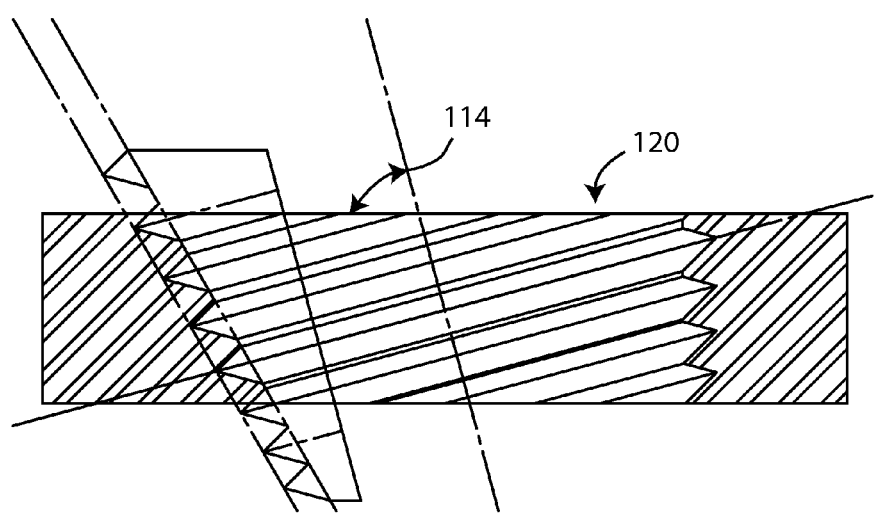
Figures 16A, 16B:
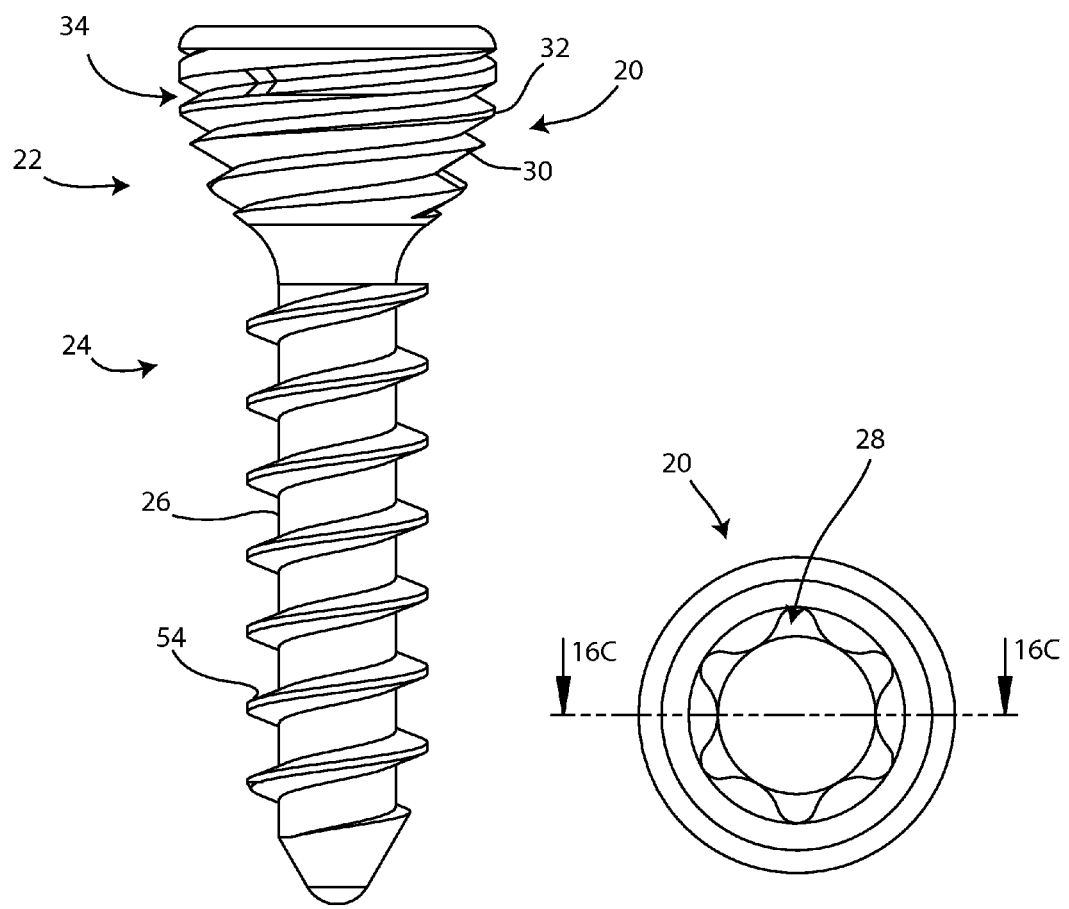
Figure 16C:
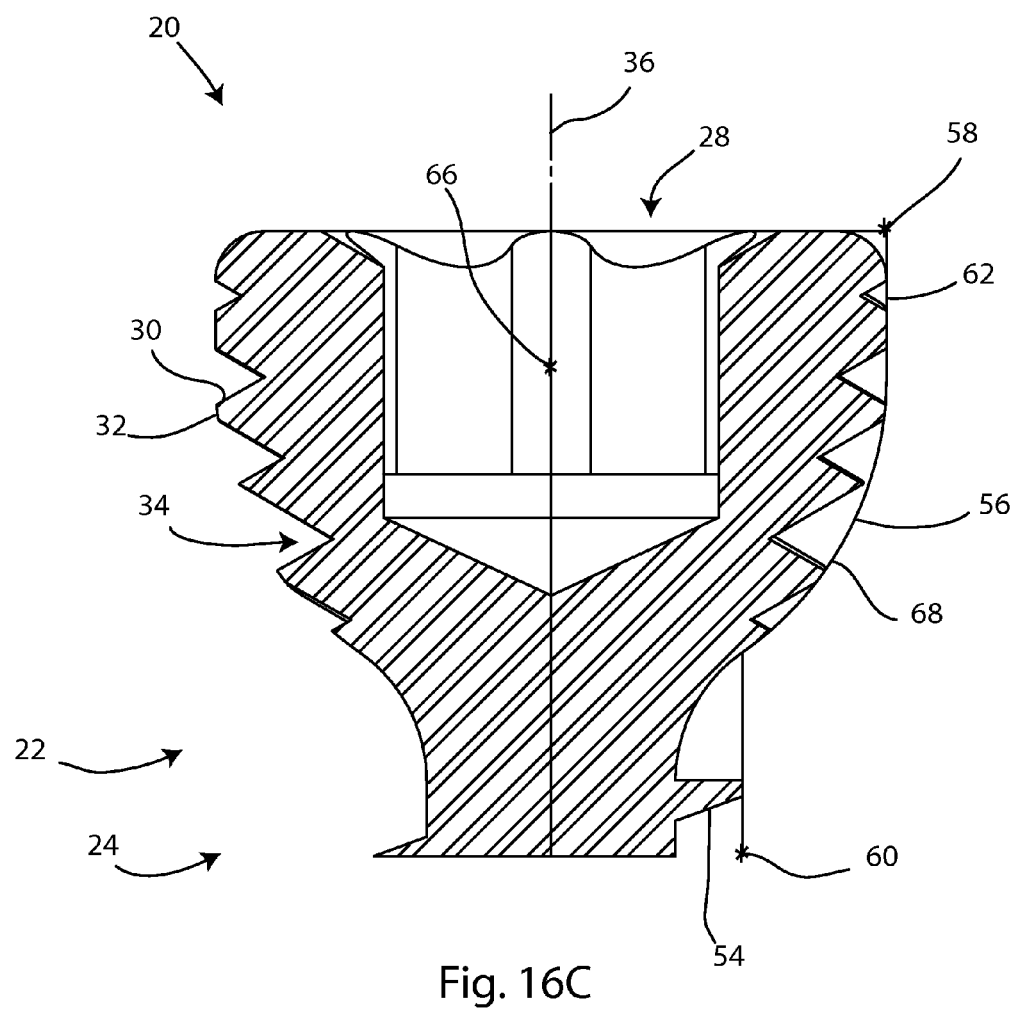
Figure 17A:
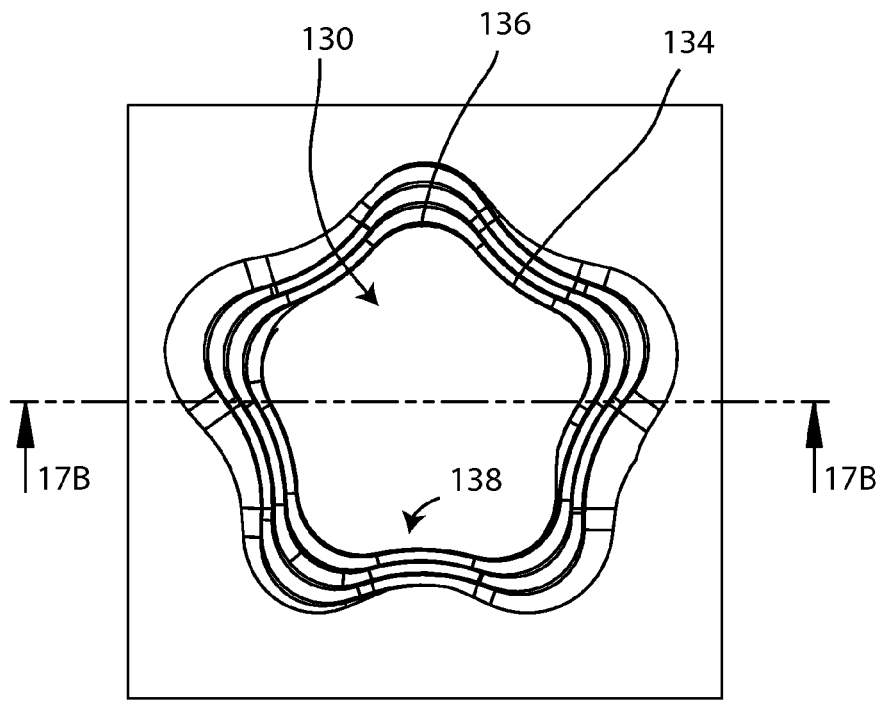
Figure 17B:
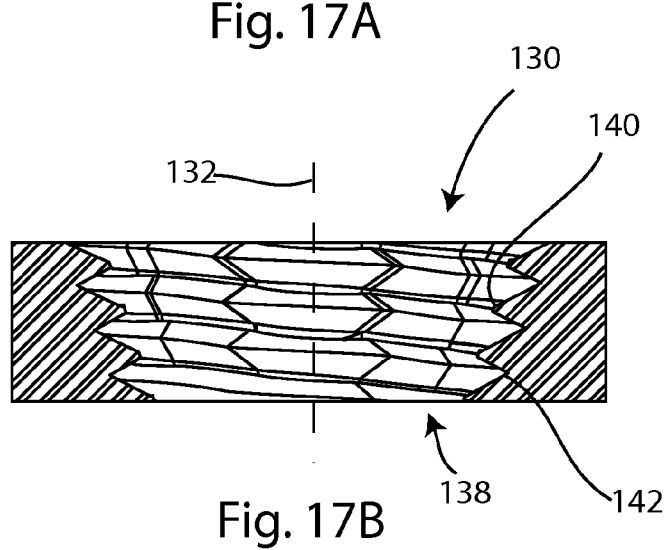
Figure 17C:
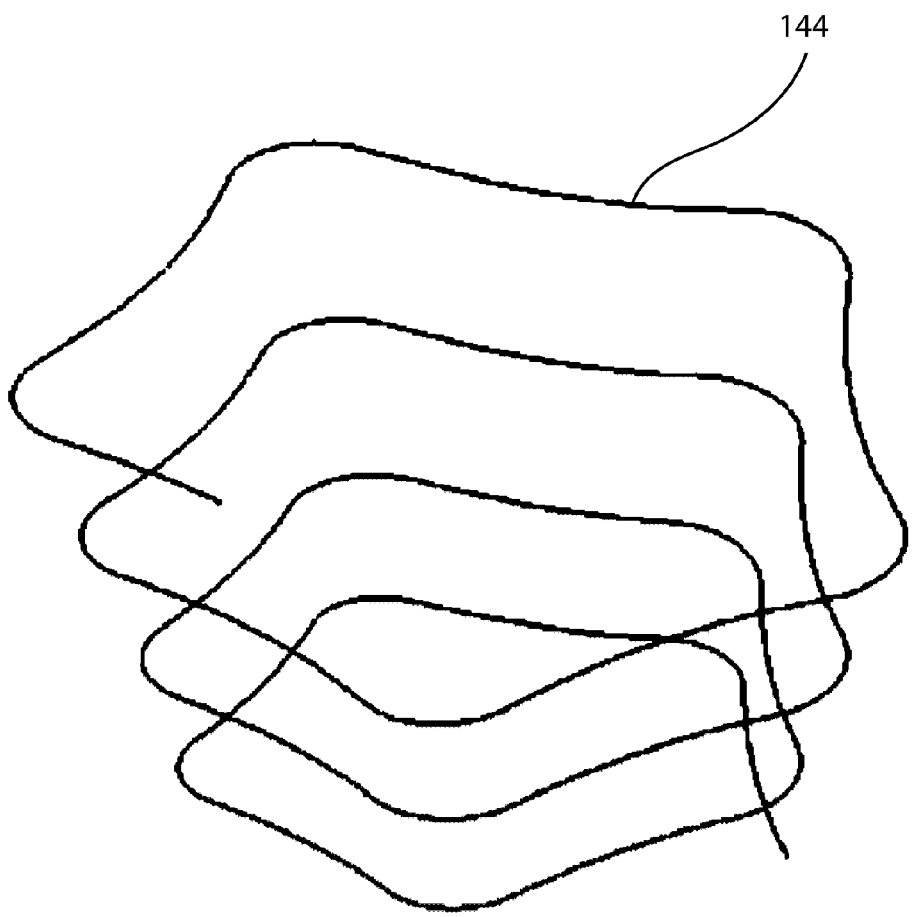
Figure 18A:
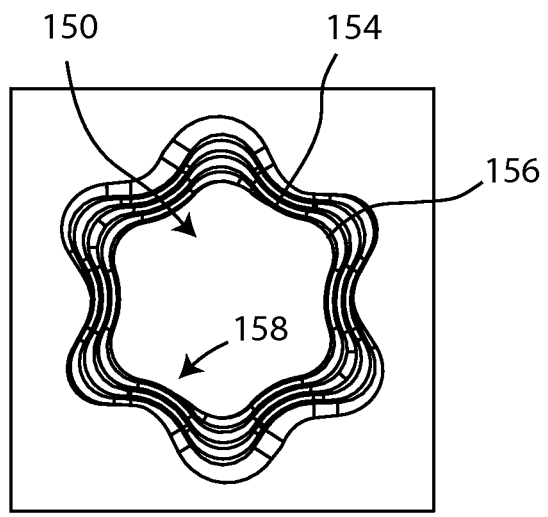
Figure 18B:
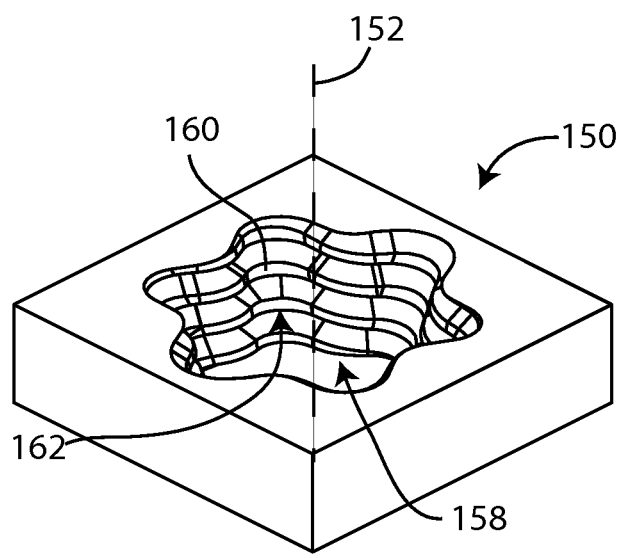

FIG. 1 is an isometric view of an interlocking interface between a screw and a socket;

FIG. 2 is an isometric exploded view of the screw and socket of FIG. 1;

FIG. 3 is a top view of the screw and socket of FIG. 1;

FIG. 4A is another top view of the screw and socket of FIG. 1; FIG. 4B is a front cross-sectional view of the screw and socket of FIG. 1, taken along section line 4B-4B of FIG. 4A, a range of positions of the screw relative to the socket is shown by dashed lines; and FIG. 4C is a front cross-sectional view of the socket of FIG. 1, also taken along section line 4B-4B of FIG. 4A;

FIG. 5 is a top view of the socket of FIG. 1;

FIG. 6 is an isometric view of another socket;

FIG. 7A is a top view of the socket of FIG. 6; and FIG. 7B is a front cross-sectional view of the socket of FIG. 6, taken along section line 7B-7B of FIG. 7A;

FIG. 8 is an isometric cross-sectional view of the socket of FIG. 6, taken along section line 7B-7B of FIG. 7A;

FIG. 9 is an isometric view of another interlocking interface between the screw and yet another socket;

FIG. 10 is an isometric exploded view of the screw and socket of FIG. 9;

FIG. 11A is a top view of the screw and socket of FIG. 9; and FIG. 11B is a compound front cross-sectional view of the screw and socket of FIG. 9, taken along section line 11B-11B of FIG. 11A, a first position of the screw shown on the left and a second position of the screw shown on the right;

FIG. 12 is a top view of the socket of FIG. 9;

FIG. 13 is a sketch of the cross-sectional geometry of the socket of FIG. 9;

FIG. 14A is another top view of the socket of FIG. 9; and FIG. 14B is a front cross-sectional view of the socket of FIG. 9, taken along section line 14B-14B of FIG. 11A;

FIG. 15A is a top view of yet another socket; and FIG. 15B is a front cross-sectional view of the socket of FIG. 15A, taken along section line 15B-15B of FIG. 15A;

FIG. 16A is a front view of the screw of FIG. 1; FIG. 16B is a top view of the screw of FIG. 1; and FIG. 16C is a front cross sectional view of the screw of FIG. 1, taken along section line 16C-16C of FIG. 16B;

FIG. 17A is a top view of yet another socket; FIG. 17B is a front cross-sectional view of the socket of FIG. 17A, taken along section line 17B-17B of FIG. 17A; and FIG. 17C is an isometric view of a sweep profile of the socket of FIG. 17A; and FIG. 18A is a top view of yet another socket; and FIG. 18B is an isometric view of the socket of FIG. 18A.

DETAILED DESCRIPTION

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

Referring to FIGS. 1-5, a locking interface 10 includes a head 20 and a socket 40.

With reference to FIGS. 1-5 and 16A-16C, the head 20 is an external feature which may be formed on any medical device component, such as a fastener, connector, rod, link, bone-contacting component, articular component, and the like. The head 20 shown in FIG. 1 is an external feature formed on a proximal end 22 of a fastener 24. The fastener 24 includes a distal portion 26 which may include bone fixation features, such as external threads, ribs, porous coating, and the like; however, for simplicity, a smooth cylindrical distal portion 26 is shown in FIGS. 1-2, and 4B; a distal portion 26 with an external thread 54 is shown in FIGS. 16A and 16C. The head 20 may include an instrument connection feature 28. The instrument connection feature 28 may be an internal or external feature; a hexagonal internal feature is shown in FIGS. 1-4A and a hexalobular internal feature is shown in FIG. 16B. The internal feature may be a slot, a cruciform indentation or Phillips socket, a polygonal indentation, a hexalobular or Torx socket, a circular hole, and the like. Any of these features may be expressed as an external feature as well. The instrument connection feature 28 may be shaped and sized for complementary connection with an instrument (not shown). The connection feature 28 may couple the head 20 to an instrument so that compressive, tensile, torque, and/or other forces may be transmitted between the head 20 and the instrument. The connection may be a slip fit, a line-to-line fit, an interference fit, an interlocking undercut fit, threads, a snap fit, a taper fit, or any other connection.

Referring to FIG. 16C, the head 20 may be formed by revolving a profile 56 about a longitudinal axis of revolution 36, which may also be described as a longitudinal axis 36 of the head 20. The revolved profile 56 may be formed by one or more lines, curves, or other two-dimensional shapes. The head 20 may be cylindrical, multi-cylindrical, frustoconical, multi-conical, spherical, cylindro-spherical, ovoid, and the like. The head 20 may also have a faceted perimeter. In the example shown in FIG. 16C, the revolved profile 56 of the head 20 extends at least between a proximal point 58 and a distal point 60 to define an outermost shape of the head 20. The illustrated profile 56 includes a proximal line segment 62 which is parallel to the axis 36, and a distal arc segment 68 which is tangent to the line segment 62. A center point 66 of the arc segment 68 may lie on the axis 36 as shown or may be offset from the axis 36. When revolved about the axis 36, arc segment 68 forms a spherical portion of the head 20 by virtue of having center point 66 on the axis 36.

The head 20 includes external corrugations 30 which may be described as forming alternating peaks 32 and valleys 34. The corrugations 30 may be formed in the head 20 so that the peaks 32 lie upon, or follow, the surface of the head. The valleys 34 may also follow the surface of the head at a fixed offset so that there is a constant valley depth. Alternately, the valleys 34 may follow at a variable offset, so that valley depth varies along the head. The peaks 32 and/or valleys 34 may be sharp or blunt. The external corrugations 30 may be intact or uninterrupted throughout their extent along the head 20.

The socket 40 is a noncircular hole, such as the rounded rectangular hole illustrated in FIGS. 1-5. The socket 40 may have a longitudinal axis 52. The socket 40 may be formed in any medical device component, such as a plate, washer, rod, link, bone-contacting component, articular component, and the like. The socket 40 may extend completely through a component, or only partially through the component. The socket 40 may be multi-sided; the example of FIGS. 1-5 has four flat sides 42 and four rounded corners 44. The socket 40 may include two or more sides in a polygonal arrangement, such as an oval, triangle, rectangle, pentagon, hexagon, heptagon, octagon, and so on. In this specification, a polygon may have sides that deviate from perfectly straight, for example by bulging or bending inward or outward. The corners 44 may be sharp or rounded. In other examples, the socket 40 may have a poly-lobular profile such as a starburst shape with three or more points or corners 44. The points 44 may be sharp or rounded, and the sides 42 may bulge toward the interior of the socket in these examples. Examples of poly-lobular profile profiles include pentagram, hexalobe, hexagram, and other star-shaped shapes. Another example may be described as a spline. The socket 40 may have a constant cross-sectional geometry over the full depth of the socket 40, as seen best in FIG. 4B. Alternatively, the socket 40 may taper or bulge along its length. The socket 40 may have a spherical or partial spherical interior. The socket 40 may twist along its depth.

The socket 40 includes an internal corrugation 46 which includes alternating peaks 48 and valleys 50 along the depth of the socket 40, or a portion thereof. The peaks 48 and/or valleys 50 may be sharp or blunt. The peaks 48 may lie upon, or follow, the interior surface of the socket 40. The valleys 50 may be described as indentations into the interior surface of the socket 40, and thus the valleys 50 may also follow the interior surface of the socket 40, albeit offset below the interior surface. The valleys 50 may follow the interior surface exactly with a constant offset, or generally, with a variable offset. The internal corrugation 46 may be intact, or uninterrupted, throughout its extent so that all of the peaks 48 and valleys 50 are intact. This configuration may reduce socket stresses compared to designs with interrupted threads or other discrete protrusions in the socket.

The internal corrugations 46 may be formed by a single indentation, or valley 50, which winds around the socket 40 while progressing longitudinally within the socket 40. This arrangement is best seen in FIG. 2. More than one indentation may be present. Additional indentations may wind around the socket 40 with the single indentation. The longitudinal progression per circuit around the socket 40 may be constant or variable.

In use, the head 20 may be inserted into the socket 40 with the axes 36, 52 aligned or coaxial. This arrangement is shown in FIGS. 1-2 and in FIG. 4B in solid lines. The external corrugations 30 of the head 20 may engage with the internal corrugation feature 46 of the socket 40 so that the peaks 32 rest in the valleys 50 and the peaks 48 rest in the valleys 34. This engagement may resemble a traditional threaded engagement. However, the incongruent shapes of the head 20 and socket 40 provide alternating zones of contact and clearance between the head 20 and the socket 40, as can be seen best in FIG. 3 with reference to FIG. 5. Contact occurs between the sides 42 and the head 20, and clearance occurs between the corners 44 and the head 20.

In another method of use, the head 20 may be inserted into the socket 40 with the axes 36, 52 misaligned. The axes 36, 52 may be intentionally or unintentionally misaligned. Two examples of this arrangement are shown in FIG. 4B in dashed lines. The external corrugations 30 of the head 20 may engage with the internal corrugation feature 46 of the socket 40 to lock the head 20 at a range of angles with respect to the socket 40. This arrangement is facilitated by the zones of contact and clearance between the head 20 and the socket 40, which permit the corrugations 30 to skip over a zone of clearance instead of encountering an interfering peak 48 in the socket. The dashed line representations in FIG. 4B show two possible angular orientations of the head 20 with respect to the socket 40 out of a range of possible angular orientations extending in a conical field around the axis 52 of the socket 40. The locking interconnection between the head 20 and the socket 40 may be described as polyaxial for this reason.

FIGS. 6-8 show another socket 70 for use with the head 20 in a polyaxial locking interconnection. Socket 70 is another noncircular hole, which may have a longitudinal axis 72. The socket 70 may be formed in any medical device component, such as a plate, washer, rod, link, bone-contacting component, articular component, and the like. The socket 70 may extend completely through a component, or only partially through the component. The socket 70 may include two or more sides in a polygonal or poly-lobular arrangement. The socket 70 may have six flat sides 74 and six rounded corners 76, however the corners 76 may be sharp instead. The socket 70 may have a constant cross-sectional geometry over the full depth of the socket 70 as seen best in FIG. 7B. Alternatively, the socket 70 may taper or bulge along its length. The socket 70 may have a spherical or partial spherical interior. The socket 70 may twist along its depth.

The socket 70 includes an internal corrugation 78 which includes alternating peaks 80 and valleys 82 along the depth of the socket 70, or a portion thereof. The peaks 80 and/or valleys 82 may be sharp or blunt. The peaks 80 may lie upon, or follow, the interior surface of the socket 70. The valleys 82 may be described as indentations into the interior surface of the socket 70, and thus the valleys 82 may also follow the interior surface of the socket 70, albeit offset below the interior surface. The valleys 82 may follow the interior surface exactly with a constant offset, or generally, with a variable offset. The internal corrugation 78 may be intact, or uninterrupted, throughout its extent so that all of the peaks 80 and valleys 82 are intact to minimize stress concentrations.

The internal corrugations 78 may be formed by a single indentation, or valley 82, which winds around the socket 70 while progressing longitudinally within the socket 70. This arrangement is best seen in FIG. 7B. More than one indentation may be present. Additional indentations may wind around the socket 70 with the single indentation. The longitudinal progression per circuit around the socket 70 may be constant or variable.

In use, the head 20 may be inserted into the socket 70 with the axes 36, 72 aligned or coaxial, or misaligned, as described above for socket 40. In either arrangement, the external corrugations 30 of the head 20 may engage with the internal corrugation feature 78 of the socket 70 to lock the head 20 at a range of angles with respect to the socket 70. The incongruent shapes of the head 20 and socket 70 provide alternating zones of contact and clearance between the head 20 and the socket 70. Contact occurs between the sides 74 and the head 20, and clearance occurs between the corners 76 and the head 20.

FIGS. 9-14B show another locking interface 90, which includes the head 20 and yet another socket 100. Socket 100 is another noncircular hole, which may have a longitudinal axis 102. The socket 100 may be formed in any medical device component, such as a plate, washer, rod, link, bone-contacting component, articular component, and the like. The socket 100 may extend completely through a component, or only partially through the component. The socket 100 may include two or more sides in a polygonal or poly-lobular arrangement. The socket 100 may have five sides 104 and five rounded corners 106, however the corners 106 may be sharp instead. The sides 104 may bulge slightly toward the interior of the socket 100. FIG. 13 shows a sketch depicting the geometry used to define the five-sided socket 100. The other sockets disclosed herein may employ similar sketches. The socket 100 may have a constant cross-sectional geometry over the full depth of the socket 100. Alternatively, the socket 100 may taper (FIGS. 11B and 14B) or bulge along its length. The socket 100 may have a spherical or partial spherical interior. The socket 100 may twist along its depth.

The socket 100 includes an internal corrugation 112 which includes alternating peaks 108 and valleys 110 along the depth of the socket 100, or a portion thereof. The peaks 108 and/or valleys 110 may be sharp or blunt. The peaks 108 may lie upon, or follow, the interior surface of the socket 100. The valleys 110 may be described as indentations into the interior surface of the socket 100, and thus the valleys 110 may also follow the interior surface of the socket 100, albeit offset below the interior surface. The valleys 110 may follow the interior surface exactly with a constant offset, or generally, with a variable offset. The internal corrugation 112 may be intact, or uninterrupted, throughout its extent so that all of the peaks 108 and valleys 110 are intact.

The internal corrugations 112 may be formed by a series of indentations, or valleys 110, which are patterned longitudinally within the socket 100. This arrangement is best seen in FIG. 14B. The longitudinal progression per valley 100 along the socket 100 may be constant or variable. FIG. 14B includes a sketch of the geometry used to define the internal corrugations 112, which illustrates a variable longitudinal progression.

In use, the head 20 may be inserted into the socket 100 with the axes 36, 102 aligned or coaxial (FIG. 11B, left), or misaligned (FIG. 11B, right), as described above for socket 40. In either arrangement, the external corrugations 30 of the head 20 may engage with the internal corrugation feature 112 of the socket 100 to lock the head 20 at a range of angles with respect to the socket 100. The incongruent shapes of the head 20 and socket 100 provide alternating zones of contact and clearance between the head 20 and the socket 100. Contact occurs between the sides 104 and the head 20, and clearance occurs between the corners 106 and the head 20.

Socket 100 may provide a more uniform polyaxial connection with the head 20 than that provided by the previous sockets 40, 70. Socket 100 is shown with five sides 104, while socket 40 is shown with four sides 42, and socket 70 is shown with six sides 74. Sockets with an even number of sides have facing sides and facing corners. The internal width of the socket is less between facing sides than it is between facing corners. The resistance to head engagement in the socket when the head is angled toward a corner is less than the resistance when the head is angled toward a side. In contrast, the socket 100 has an odd number of sides. Each side 104 faces a corner 106. The resistance to head engagement may be less directional for socket 100 than for sockets 40 or 70.

FIGS. 15A-B show yet another socket 120 for use with the head 20 in a polyaxial locking interconnection. Socket 120 illustrates a principle that applies to any of the sockets disclosed herein. The sockets 40, 70, and 100 are all shown extending perpendicular to, or normal to, a device surface surrounding the socket. It will be appreciated that this is a design convenience. Any of the sockets disclosed herein may extend into a device at an acute angle which, in this specification, is defined as an angle which is greater than zero degrees and less than ninety degrees. FIG. 15A-B show that socket 120 extends into a device at an acute angle 114. Otherwise, socket 120 is the same as socket 100, and may provide the same advantages with regard to uniform head 20 insertion effort at various head insertion angles.

FIGS. 17A-17C show yet another socket 130 for use with head 20. Socket 130 is another noncircular hole, which may have a longitudinal axis 132. The socket 130 may be formed in any medical device component, such as a plate, washer, rod, link, bone-contacting component, articular component, and the like. The socket 130 may extend completely through a component, or only partially through the component. The socket 130 may include two or more sides in a polygonal or poly-lobular arrangement. The socket 130 may have five sides 134 and five rounded corners 136, however the corners 136 may be sharp instead. The sides 134 may bulge toward the interior of the socket 130. The socket 130 may have a constant cross-sectional geometry over the full depth of the socket 130. Alternatively, the socket 130 may taper (FIG. 17B) or bulge along its length. The socket 130 may have a spherical or partial spherical interior. The socket 130 may twist along its depth.

The socket 130 includes an internal corrugation 138 which includes alternating peaks 140 and valleys 142 along the depth of the socket 130 or a portion thereof. The peaks 140 and/or valleys 142 may be sharp or blunt. The peaks 140 may lie upon, or follow, the interior surface of the socket 130. The valleys 142 may be described as indentations into the interior surface of the socket 130, and thus the valleys 142 may also follow the interior surface of the socket 130, albeit offset below the interior surface. The valleys 142 may follow the interior surface exactly with a constant offset, or generally, with a variable offset. The internal corrugation 138 may be intact, or uninterrupted, throughout its extent so that all of the peaks 140 and valleys 142 are intact.

The internal corrugations 138 may be formed by a single indentation, or valley 142, which winds around the socket 130 while progressing longitudinally within the socket 130. This arrangement is best seen in FIG. 17B. More than one indentation may be present. Additional indentations may wind around the socket 130 with the single indentation. The longitudinal progression per circuit around the socket 130 may be constant or variable. FIG. 17C shows a sketch depicting a sweep profile 144 for the corrugation 138. Sockets 40, 70 may each employ a similar sweep profile for the corrugations 46, 78. Where more than one indentation is present, a similar number of sweep profiles may be included.

In use, the head 20 may be inserted into the socket 130 with the axes 36, 132 aligned or coaxial, or misaligned, as described above for socket 40. In either arrangement, the external corrugations 30 of the head 20 may engage with the internal corrugation feature 138 of the socket 130 to lock the head 20 at a range of angles with respect to the socket 130. The incongruent shapes of the head 20 and socket 130 provide alternating zones of contact and clearance between the head 20 and the socket 130. Contact occurs between the sides 134 and the head 20, and clearance occurs between the corners 136 and the head 20. Socket 130 may provide the same advantages with regard to uniform head 20 insertion effort at various head insertion angles as does socket 100.

FIGS. 18A-18B show yet another socket 150 for use with the head 20 in a polyaxial locking interconnection. Socket 150 is another noncircular hole, which may have a longitudinal axis 152. The socket 150 may be formed in any medical device component, such as a plate, washer, rod, link, bone-contacting component, articular component, and the like. The socket 150 may extend completely through a component, or only partially through the component. The socket 150 may include two or more sides in a polygonal or poly-lobular arrangement. The socket 150 may have six sides 154 and six rounded corners 156, however the corners 156 may be sharp instead. The sides 154 may bulge toward the interior of the socket 150. The socket 150 may have a constant cross-sectional geometry over the full depth of the socket 150. Alternatively, the socket 150 may taper (FIG. 18A) or bulge along its length. The socket 150 may have a spherical or partial spherical interior. The socket 150 may twist along its depth.

The socket 150 includes an internal corrugation 158 which includes alternating peaks 160 and valleys 162 along the depth of the socket 150 or a portion thereof. The peaks 160 and/or valleys 162 may be sharp or blunt. The peaks 160 may lie upon, or follow, the interior surface of the socket 150. The valleys 162 may be described as indentations into the interior surface of the socket 150, and thus the valleys 162 may also follow the interior surface of the socket 150, albeit offset below the interior surface. The valleys 162 may follow the interior surface exactly with a constant offset, or generally, with a variable offset. The internal corrugation 158 may be intact, uninterrupted, throughout its extent so that all of the peaks 160 and valleys 162 are intact.

The internal corrugations 158 may be formed by a single indentation, or valley 162, which winds around the socket 150 while progressing longitudinally within the socket 150. This arrangement is best seen in FIG. 19B. More than one indentation may be present. Additional indentations may wind around the socket 150 with the single indentation. The longitudinal progression per circuit around the socket 150 may be constant or variable.

In use, the head 20 may be inserted into the socket 150 with the axes 36, 152 aligned or coaxial, or misaligned, as described above for socket 40. In either arrangement, the external corrugations 30 of the head 20 may engage with the internal corrugation feature 158 of the socket 150 to lock the head 20 at a range of angles with respect to the socket 150. The incongruent shapes of the head 20 and socket 150 provide alternating zones of contact and clearance between the head 20 and the socket 150. Contact occurs between the sides 154 and the head 20, and clearance occurs between the corners 156 and the head 20. Socket 150 may provide the same advantages with regard to uniform head 20 insertion effort at various head insertion angles as does socket 100.

While the present disclosure has been made with reference to regularly shaped sockets 40, 70, 100, 120, 130, 150, these sockets may also be irregularly formed so that the spacing and size of each feature in a socket may be different. For example, each corner may have a unique radius. This applies to each feature described and shown herein. Any of the sockets disclosed herein may transform over its length from a first polygon shape to a second shape. The second shape may be a different polygon shape, a circle, or another profile.

The components disclosed herein may be fabricated from metals, alloys, polymers, plastics, ceramics, glasses, composite materials, or combinations thereof, including but not limited to: PEEK, titanium, titanium alloys, commercially pure titanium grade 2, ASTM F67, Nitinol, cobalt chrome, stainless steel, ultra high molecular weight polyethylene (UHMWPE), biocompatible materials, and biodegradable materials, among others. Different materials may be used for different parts. Coatings may be present. Different materials may be used within a single part. Any component disclosed herein may be colored, coded or otherwise marked to make it easier for a user to identify the type and size of the component, the setting, the function(s) of the component, and the like.

It should be understood that the present systems, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several examples for the purpose of streamlining the disclosure. This method of disclosure is not to be interpreted as reflecting an intention that the examples of the invention require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

The invention claimed is:

1. A locking connection comprising:
   a polygonal socket comprising internal corrugations, wherein the polygonal socket comprises a plurality of sides and a corresponding plurality of corners, wherein the sides bulge toward an interior of the socket; and
   a head received in the socket, the head comprising external corrugations;
   wherein the external corrugations engage the internal corrugations at any of a plurality of orientations of the head relative to the socket.

2. The locking connection of claim 1, wherein the polygonal socket includes five corners.

3. The locking connection of claim 1, wherein the internal corrugations are uninterrupted throughout the socket.

4. The locking connection of claim 1, wherein the internal corrugations are patterned longitudinally within the polygonal socket.

5. The locking connection of claim 1, wherein a longitudinal progression of corrugations along the socket is variable.

6. The locking connection of claim 1, wherein the internal corrugations comprise alternating peaks and valleys, wherein the valleys follow an interior surface of the socket with a variable offset below the interior surface of the socket.

7. The locking connection of claim 1, wherein the polygonal socket includes an odd number of corners.

8. A locking connection comprising:
   a polygonal socket comprising alternating internal peaks and valleys, wherein the polygonal socket comprises a plurality of sides and a corresponding plurality of corners, wherein the sides bulge toward an interior of the socket; and
   a head coupled to the socket, the head comprising alternating external peaks and valleys;
   wherein the external peaks and valleys engage the internal peaks and valleys at any of a plurality of angles of the head relative to the socket.

9. The locking connection of claim 8, wherein the polygonal socket includes five corners.

10. The locking connection of claim 8, wherein the internal peaks and valleys extend intact throughout the socket.

11. The locking connection of claim 8, wherein the internal valleys are patterned longitudinally within the polygonal socket.

12. The locking connection of claim 8, wherein a longitudinal progression of internal valleys along the socket is variable.

13. The locking connection of claim 8, wherein the internal valleys follow an interior surface of the socket with a variable offset below the interior surface of the socket.

14. The locking connection of claim 8, wherein the polygonal socket includes an odd number of corners.

15. A locking connection comprising:
   a polygonal socket comprising a first internal indentation which winds around the socket while progressing longitudinally within the socket, wherein the polygonal socket comprises a plurality of sides and a corresponding plurality of corners, wherein the sides bulge toward an interior of the socket; and
   a head coupled to the socket, the head comprising external corrugations;
   wherein the external corrugations engage the first internal indentation at any of a plurality of angles of the head relative to the socket.

16. The locking connection of claim 15, wherein the polygonal socket includes five corners.

17. The locking connection of claim 15, wherein the first internal indentation is uninterrupted throughout the socket.

18. The locking connection of claim 15, wherein the polygonal socket is longitudinally tapered.

19. The locking connection of claim 15, wherein a longitudinal progression of the first internal indentation per circuit around the polygonal socket is variable.

20. The locking connection of claim 15, comprising a second internal indentation which winds around the socket with the first internal indentation.

21. The locking connection of claim 15, wherein the first internal indentation follows an interior surface of the socket with a variable offset below the interior surface of the socket.

22. The locking connection of claim 15, wherein the polygonal socket includes an odd number of corners.

* * * * *